United States Patent [19]

Grussmark

[11] Patent Number: 4,836,415
[45] Date of Patent: Jun. 6, 1989

[54] DENTAL TIMER

[76] Inventor: Stephen M. Grussmark, 2901 S. Bayshore Dr., #15C, Coconut Grove, Fla. 33134

[21] Appl. No.: 115,803

[22] Filed: Nov. 2, 1987

[51] Int. Cl.⁴ .............................................. B67D 5/32
[52] U.S. Cl. ...................................... 222/39; 222/638; 222/192; 206/216; 340/309.4; 340/309.15; 368/10
[58] Field of Search ................. 222/192, 638, 106, 39; 116/308, 307; 221/2, 15; 132/84 R, 79 E, 84 D; 340/309.15, 309.4; 206/216; 368/10, 109, 250, 1, 93

[56] References Cited

U.S. PATENT DOCUMENTS

| | | | |
|---|---|---|---|
| 1,923,978 | 8/1933 | Hill | 368/10 |
| 1,973,390 | 9/1934 | Plants | 368/93 |
| 2,824,418 | 2/1958 | Hilbert | 368/93 |
| 3,129,845 | 4/1964 | Musser | 222/638 X |
| 3,542,519 | 11/1970 | Montalto et al. | 132/84 R |
| 3,783,364 | 1/1974 | Gallanis et al. | 368/10 X |
| 3,803,579 | 4/1974 | Compton | 340/309.15 |
| 4,010,869 | 3/1977 | Adamo | 221/15 |
| 4,361,408 | 11/1982 | Wirtschafter | 222/638 X |
| 4,367,955 | 1/1983 | Ballew | 368/10 |
| 4,382,688 | 5/1983 | Machamer | 340/309.4 X |
| 4,448,541 | 5/1984 | Wirtschafter | 368/10 |
| 4,673,106 | 6/1987 | Fishman | 222/192 X |

Primary Examiner—Joseph J. Rolla
Assistant Examiner—Gregory L. Huson
Attorney, Agent, or Firm—Malloy, John Cyril

[57] ABSTRACT

A toothpaste dispenser with a timer device so that a person will receive a signal to indicate the time period during which the teeth are being brushed; three embodiments are shown, in one embodiment an hourglass timer is provided and in a second and third embodiment an electrical signal device is provided the timing being selected of a time period of between two and three minutes, the optimal period during which brushing should continuously be done in a tooth cleaning operation in order to achieve maximum results.

1 Claim, 1 Drawing Sheet

DENTAL TIMER

BACKGROUND OF THE INVENTION

1. Field of the Invention

This invention relates to a toothpaste dispenser in combination with the timer means to indicate to a person using the same the amount of time required to brush ones teeth properly.

In the past there have been numerous types of timer means which have been available for attachment to various devices and which indicate the expenditure of a certain period of time. This invention is of the combination of a timer means together with a toothpaste dispenser so that the timer means is actuated for the user when the toothpaste is dispensed and a predetermined period of time is then indicated to him either visually or audibly so that the user will be encouraged to brush his teeth for the proper indicated period of time.

2. Description of the Prior Art

Representative of prior art is found in U.S. Pat. No. 1,080,464 which is of a poison bottle with a bell attached to it comprising a signal means.

U.S. Pat. No. 628,472 is of a mechanical time alarm for use in combination with a telephone. There is a safety attachment for a bottle shown in U.S. Pat. No. 358,434 which is especially adaptable for containers containing poisonous substance and provides an alarm when the stopper of the bottle is withdrawn. Representative of additional prior art is shown immediately in U.S. Pat. No. 410,730 and in the telephone timer of U.S. Pat. No. 3,146,577. However, there is no teaching in the prior art of a timer mechanism and a dispenser used in combination so that a person will receive a signal that will indicate a time period during which the person should continue brushing ones teeth.

OBJECTS OF THE PRESENT INVENTION

It is an object of this invention to provide a toothpaste dispenser in combination with a timer means which is adapted to be actuated when the toothpaste is dispensed onto the toothbrush of a user so that, after a minimum predetermined period of time, the user will know that he has brushed his teeth an optimum amount of time and may discontinue the operation. This is especially useful for children who are being taught the necessity of good tooth cleansing operation.

DESCRIPTION OF THE PREFERRED EMBODIMENT

Figure 1:
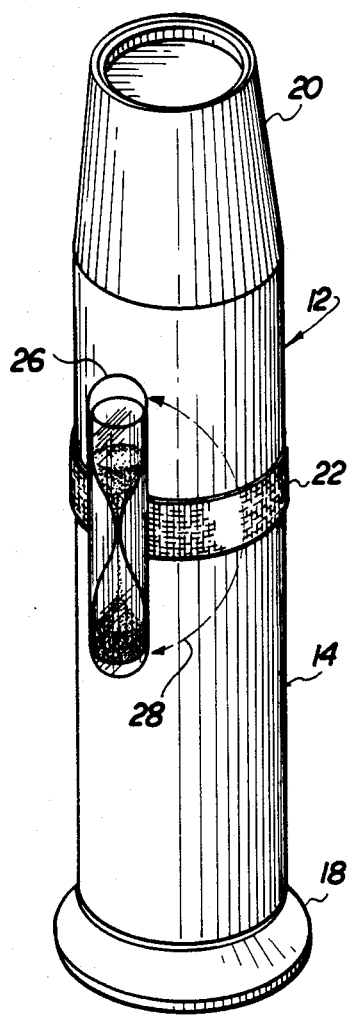
FIG. 1 is a side elevation view of a toothpaste dispenser illustrating one embodiment of the instant invention.
Figure 3:
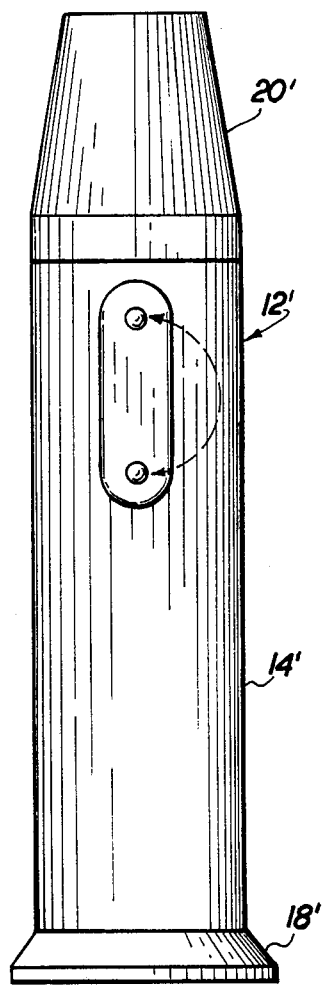
FIG. 3 is a side elevation view of an alternative embodiment of the instant invention.
Figure 6:
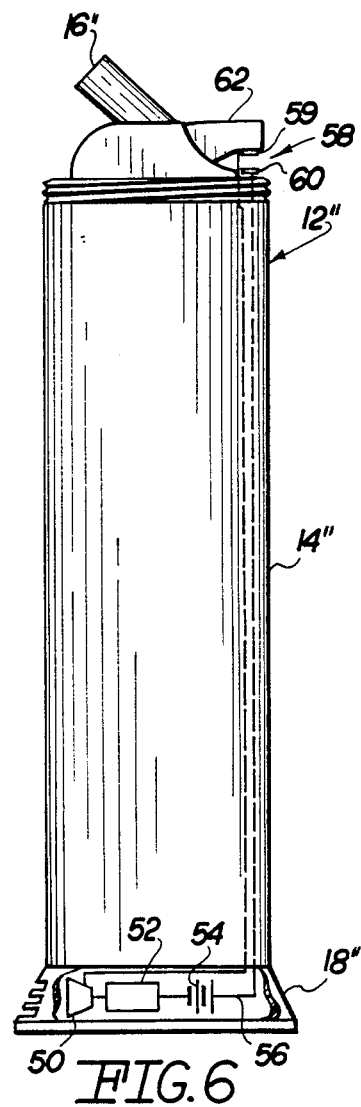

Referring now to the drawings wherein like reference characters designate like or corresponding parts throughout the several views and referring generally, to FIGS. 1, 3 and 6, it is seen that there is provided a toothpaste dispenser 12, 12' and 12" which, in general, is commercially available and well known in the market place, including a main body tubular length 14, 14' and 14" in which the charge of toothpaste is arranged and which includes some commercially available dispensing mechanism so that from the dispensing tip, see FIG. 6, at 16' toothpaste is emitted. Conventionally the toothpaste dispensers are provided with a base 18, 18' and 18" and a cap, such as 20 and 20' in Figures 1 and 3 respectively. In use, the cap is removed, toothpaste is dispensed through the opening such as at 16" and a person brushes their teeth. In the tooth cleaning operation, it is well known that a person, in order to secure the maximum benefits, should brush his teeth a minimum of two minutes to three minutes. Most persons are notoriously incapable of estimating such a time period. This invention, therefore, provides a timer means in combination with the toothpaste dispenser so that a person is provided with a signal to indicate the time period during which the teeth are being brushed. In the following description, three embodiments are illustrated: First, what may be described as a mechanical timer, a simple hourglass, which, when brushing is initiated, is rotated through 180 degrees so that when the sands have passed through to the lower portion of the hourglass the tooth cleaning operation has proceeded a sufficient length of time. Further embodiments include an electrical tilt actuated switch type, see FIG. 3, and an electric signal means including a timer means as in the embodiment of Figure 6. These embodiments will now be described in more detail, but, first, it should be pointed out that other types of timer means may be utilized. For example, there may be an annular timer means about the toothpaste dispenser and mechanically capable of being twisted through a angular displacement range so that while the teeth are being brushed, the timer winds down and gives a signal when there has been sufficient brushing activity. Alternatively, a plunger type of timer may be utilized such that, when the toothpaste is emitted brushing is initiated, that is when one pushes down on the plunger, energy is stored in a spring means which is gradually released until the time period has been completed which is most beneficial for brushing you teeth.

Figure 2:
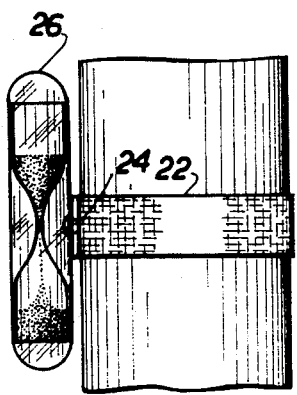
FIG. 2 is a partial side elevation of the timer means and a portion of the dispenser seen in FIG. 1.

In a first preferred embodiment as shown in FIGS. 1 and 2, it is seen that a band 22 may be provided about the tubular length of the toothpaste dispenser and comprises pivot means 24 to mount together and interconnect the band 22 and an hourglass structure 26. Alternately, the structure 26 may be mounted directly on the dispenser. In use with this embodiment, when the brushing operation is commenced, the user merely rotates the timer means, as indicated by the arrowed line 28, through 180 degrees of rotation and brushes his teeth until the predetermined time has expired. The predetermined time is measured by the time required for the sands to move through the hourglass structure.

Figure 4:
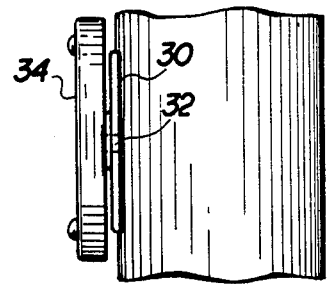
FIG. 4 is a partial side elevation of the timer means and a portion of the toothpaste dispenser seen in FIG. 3.
Figure 5:
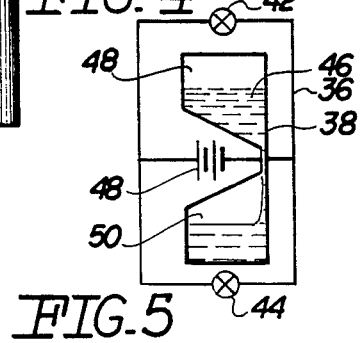
FIG. 5 is a schematic view illustrating a tilt actuated mercury switch which is included in the embodiment of FIGS. 3 and 4; and, FIG. 6 is a side elevation view which has been partially broken away at the lower end thereof and which schematically illustrates a toothpaste dispenser having a dispensing lever at the top with switch contacts on the lever and the dispenser adaptive for electrical engagement with one another when the lever is depressed to actuate a circuit which may be contained in the base and which includes a battery, timer circuit and electrical signal means in series with said switch contacts.

Referring to the second alternative embodiment as shown in FIGS. 3, 4 and 5, an alternative timer means is illustrated. In this embodiment, a toothpaste dispenser body 14' is shown in which there is mounted to the body thereof, as by an adhesive means 30, a pad which provides a pivotal means 32 for connecting a tilt actuated switch 34 thereto. The tilt actuated switch comprises a circuit generally indicated in FIG. 5 by the numeral 36 and which includes, in series, a tilt actuated mercury switch 38, a battery 48', and circuit means including electric signal means 42 and 44 which are in parallel with one another. In the embodiment shown the mercury 46 is housed in a chamber which has two main portions, 48 and 50, on opposite sides of the circuit connecting the battery and the light means. The mercury is adapted, when in the upper most chamber as at 48, to flow slowly downward into the lower chamber as at 50 and while doing so maintaining conductive contact with opposite sides of the circuit allowing the battery to energize the lights 42 and 44. While this occurs over a predetermined period of time of about two to three minutes, the minimum optimum time for which brushing operations should continue, the lights are energized. When the mercury has moved into the lower chamber, the circuit is broken, the lights go off, and the person has an indication that he need no longer continue the brushing operation.

Referring to FIG. 6, a third alternative embodiment is illustrated having circuit and electric signal means housed, for example, in the base of the dispenser. The third alternative embodiment comprises an electrically actuated signal means 50, a time delay circuit 52 and a battery means 54 in a circuit 56 which includes a switch means generally indicated at 58 composed of a first switch contact 59 and a second switch contact 60. In operation, when the lever 62 is depressed to cause toothpaste to be emitted through the opening 16", electrical contact is made between the switch contacts 59 and 60 which energizes a circuit permitting energy to flow from the battery 54 through the circuit 56 and to a time delay circuit means 52. Then, after a predetermined period of time, the electric signal 50 is energized, (which may be an audible signal) and the user can discontinue brushing operations.

In general it has thus been shown and described the invention of a toothpaste dispenser and timer means in combination so that a person using the same is provided with a signal to indicate the time period during which the teeth have been brushed thereby establishing a minimum amount of brushing time. It will be apparent that numerous types of structure may be utilized to embody this concept which is generally illustrated in the drawings and above description. While this invention has been shown and described in three practical and preferred embodiments, it is recognized that numerous other types of structures such as an annular timer mechanism with an actuating operator to be depressed may be employed. The general concept, however, is of a timer means in combination with the toothpaste dispenser wherein the timer means is actuated for a predetermined time causing a signal to be emitted so that the person will be able to measure the time from the dispensing of the toothpaste to a minimum period of time during which the teeth should be brushed for optimal results.

Now that the invention has been described,
What is claimed is:

1. A toothpaste dispenser and timer means in combination whereby a person is provided with a signal to indicate the time period during which the teeth are being brushed; and, said toothpaste dispenser including a dispenser lever means to selectively cause discharge of toothpaste from said dispenser, whereby said dispenser and said dispensing lever each include switch contacts arranged and positioned so that when the lever is depressed, said contacts are in electrical engagement with one another, and further, circuit means including said switch contacts and (a) battery means, (b) electronic timer means, and (c) signal means in series with one another whereby, when said switch contacts are in electrical engagement with one another the circuit is closed and a signal is emitted after a time delay of predetermined length.

* * * * *